United States Patent
Handschuck et al.

[11] Patent Number: 5,869,343
[45] Date of Patent: Feb. 9, 1999

[54] METHOD AND APPARATUS FOR THE AUTOMATED TESTING OF THE FLASH POINT

[75] Inventors: Bernhard Handschuck; Helmut Eilers, both of Berlin, Germany

[73] Assignee: Petrotest Instruments GmbH & Co. KG, Germany

[21] Appl. No.: 807,136

[22] Filed: Feb. 27, 1997

[30] Foreign Application Priority Data

Feb. 28, 1996 [DE] Germany .................. 196 09 413.5

[51] Int. Cl.⁶ .................. G01N 33/00; G01N 21/72
[52] U.S. Cl. .................. 436/143; 436/155; 436/156; 73/36; 374/8
[58] Field of Search .................. 436/143, 155, 436/156, 181, 183; 73/36; 374/8

[56] References Cited

U.S. PATENT DOCUMENTS 4,831,559  5/1989  Miller ...................................... 374/8 X

OTHER PUBLICATIONS

E. Bobsin *G–I–A–Fachz. Lab.* 1965, 9, 667–672.
G. Lunge *Erdoel Kohle, Erdgas, Petrochem.* 1968, 21, 224–227.
L.H. Bell *J. Inst. Petrol. London* 1971, 57,219–230.
E. Bobsin *Erdoel Kohle, Erdgas, Petrochem.* 1971, 24,553–556.
H.A. Wray *J. Paint Technol.* 1973, 45,44–50.
R.C. Lance et al. *J. Hazard, Mater.*, 1979, 3,107–119.
I.N. Rudoi et al. *Khim. Tekhnol. Topl. Masel* 1983, 41–42.
J.S. Namnath *ASTM Spec. Tech. Publ.* 1993, 1146, 180–187.
J.M. Andrade et al. *Fuel* 1993, 72,251–255.
"Standard Test Method for Flash Point by Tag Closed Tester"; The American Society for Testing and Materials Designation: D 56 –87 published Feb. 1988; pp. 1–6.

*Primary Examiner*—Arlen Soderquist
*Attorney, Agent, or Firm*—Londa and Traub LLP

[57] ABSTRACT

The invention describes a method and an apparatus for the automated testing of the flash point and can be used for determining the flash point of flammable liquids. In particular, the inventive method makes is possible to automate the phase of preparing and changing the samples. The apparatus described is characterized in that the whole of the test equipment (1) consists of a stationary simultaneous function head (2) and a mobile test insert (3), which can be separated completely from the simultaneous function head (2), the test insert (3), pre-installed, having the temperature sensor (4) and the flash point indicator (5) and contacting elements (6) for producing the electrical connection to the temperature sensor (4) and to the flash point indicator (5) and at least one coupling element (10) for producing the mechanical connection between a stirrer driving mechanism (7) and the stirrer (8) being disposed at the simultaneous function head (2). The arrangement of an additional flash point indicator (5*a*) outside of the test insert (3) is possible.

10 Claims, 2 Drawing Sheets

METHOD AND APPARATUS FOR THE AUTOMATED TESTING OF THE FLASH POINT

BACKGROUND OF THE INVENTION

The invention relates to a method and an apparatus for the automated testing of the flash point in the closed crucible and can be used to determine the flash point of flammable liquids, liquids with suspended solids, lubricating oils, liquids, which tend to form a surface film under experimental conditions, and other liquids.

The determination of the flash point of a liquid is an important criterion for assessing whether a material is a fire or explosion risk. The flash point is the lowest temperature, corrected to a barometric pressure of 101.3 kPa, at which the vapors of a sample will be ignited by an igniting flame under the specified experimental conditions. Flash point test equipment was standardized internationally, in order to make these flash point determinations comparable, even when they are made at different sites.

For this purpose, the methods of Pensky Martens (such as those of DIN 51758, ASTM D 93, ISO/EN 2719), Abel (such as those of IP 113, ISO 13726), Abel Pensky (such as those of DIN 51755/53213) and Tag (such as that of ASTM D56) with a closed test insert, are the most widespread worldwide at the present time because of the good reproducibility. All of the important instrument dimensions, such as the heating and measuring conditions, are set down in these standards. In this connection, an important instrument element is the test insert, consisting of crucible and closing lid with a rotary slide valve for freeing the openings of the test lid for an igniter dipping into the vapor space.

Pursuant to the known state of the art, the flash points, because of the rationalization required, are determined predominantly with automated equipment. It is a disadvantage of the known methods that the automation extends only to the heating process, the ignition attempts and the determination of the flash point and only inadequately to the preparatory phase of changing the sample.

SUMMARY OF THE INVENTION

It is therefore an object of the invention to provide a method and an apparatus, with which a simpler and more rapid sample change becomes possible, manual activities and subjective effects on the preparation and implementation of the flash point testing can be largely reduced and the manufacture, operation and maintenance of the apparatus can be carried out simply, reliably and at an attractive price.

It is an essential advantage of the invention that, due to the use of a simultaneous function head, the manual activities, required for changing samples in otherwise automated equipment, can be largely reduced and operator-dependent effects avoided, in that the test vessels are filled with the test liquids to begin with and closed off with test lids, having means for determining the temperature and indicating the flash point as well as means for rotating the test lids and for mixing thoroughly, to form test inserts which, so prepared, are inserted into the thermostatting equipment and the detachable connections and/or contacting between a simultaneous function head of automatic equipment and the test insert is produced in such a manner, that the means for determining the temperature and for indicating the flash point are electrically contacted and the means for mixing and rotating the test lid are optionally connected mechanically with driving mechanisms and, after ignition is accomplished and the flash point testing is concluded, the connections and/or contacts are undone once again.

Owing to the fact that the insertion of the temperature sensor as well as of the flash point indicator is advanced to the time after the filling by the sample and before the introduction into the heater, the later time section of the sample change in the automated equipment is not burdened. The manual manipulations, previously required according to the state of the art, are replaced by a single swinging in of the simultaneous function head. Since the test insert, charged with the test liquid, is essentially sealed against inadvertent evaporation of the flammable portion of the test liquid, the completely new possibility now arises of letting the prepared test insert sit even for a prolonged time and optionally pre-cooled.

If now this test insert is inserted into the thermostatting equipment, the closed state is maintained continuously up to the first standard ignition test. Due to the fact that several samples, so prepared, are kept in readiness manually or also automatically, appreciably more time is saved.

An apparatus, which complies with national and international standards, can be produced easily and inexpensively and operated reliably reproducibly, is realized owing to the fact that the whole of the test equipment consists of a stationary simultaneous function head and a mobile test insert, which can be separated from the simultaneous function head completely, the test insert, pre-installed, having at least one temperature sensor and at least one flash point indicator and contacting elements for producing the electrical connection to the temperature sensors and the flash point indicators and at least one coupling element for producing the mechanical connection between a stirrer driving mechanism and the stirrer being disposed at the simultaneous function head.

BRIEF DESCRIPTION OF THE DRAWINGS

The invention is described in greater detail below by means of examples, some of which are shown in the drawing, in which.

DETAILED DESCRIPTION OF THE INVENTION

Figure 1:
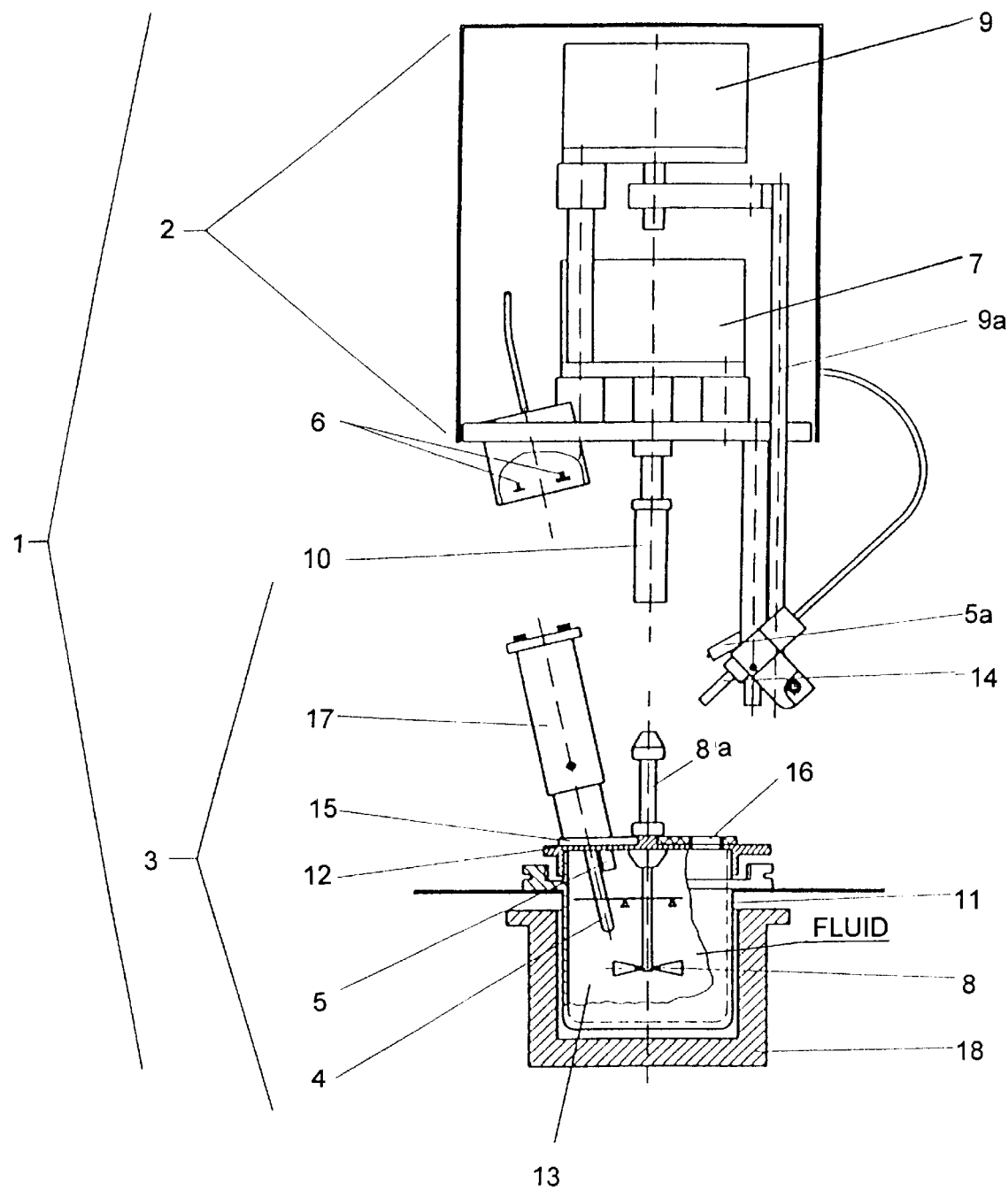
FIG. 1 shows a diagrammatic representation of the whole of the apparatus with the simultaneous function head separated from the test insert (sample-loading phase)

As can be seen from FIG. 1, the test apparatus 1 as a whole comprises a stationary simultaneous function head 2, which is connected with a control and evaluating unit (not shown in the Figures), as well as a mobile test insert 3, which is separated completely from the simultaneous function 2 in the sample loading phase.

The mobile test insert 3 consists of test vessel 11, in which there is the test liquid 13 and which is closed off by a test lid 12. A stirrer 8 dips into the test liquid 12. In the present example, the test lid 12 is equipped with a rotary slide valve 15, which serves for opening and closing the ignition opening 16. Furthermore, a sleeve 17, which serves to accommodate at least one temperature sensor 4 and at least one flash point indicator 5, is disposed at the test lid 12. The electrical contacts from the temperature sensor 4 and from the flash point indicator 5 are disposed on the sleeve 17. The temperature sensor 4 extends through the bottom of the sleeve 17 as far as into the test liquid 13 and the flash point indicator 5 extends as far as into the space above the test liquid 13. Of course, it is also possible to dispose the temperature 4 and the flash point indicator 5 directly without a sleeve 17 and to provide them with suitable contacts. The drive shaft 8a for the stirrer 8 is passed through the test lid 12. The test insert 3 is inserted in thermostatting equipment 18, in which heating or, for certain applications, also cooling is realized.

In the present example, the simultaneous function head 2 has contact elements 6, which are constructed for interaction with the contacts of the temperature sensor 4 and of the flash point indicator 5. The simultaneous function head 2 furthermore contains a stirrer driving mechanism 7, which is provided with a coupling element 10 for the mechanical coupling to the drive shaft 8a of the stirrer 8. A rotary slide valve driving mechanism 9 with an element 9a for manipulating the rotary slide valve 15 is disposed.

Figure 2:
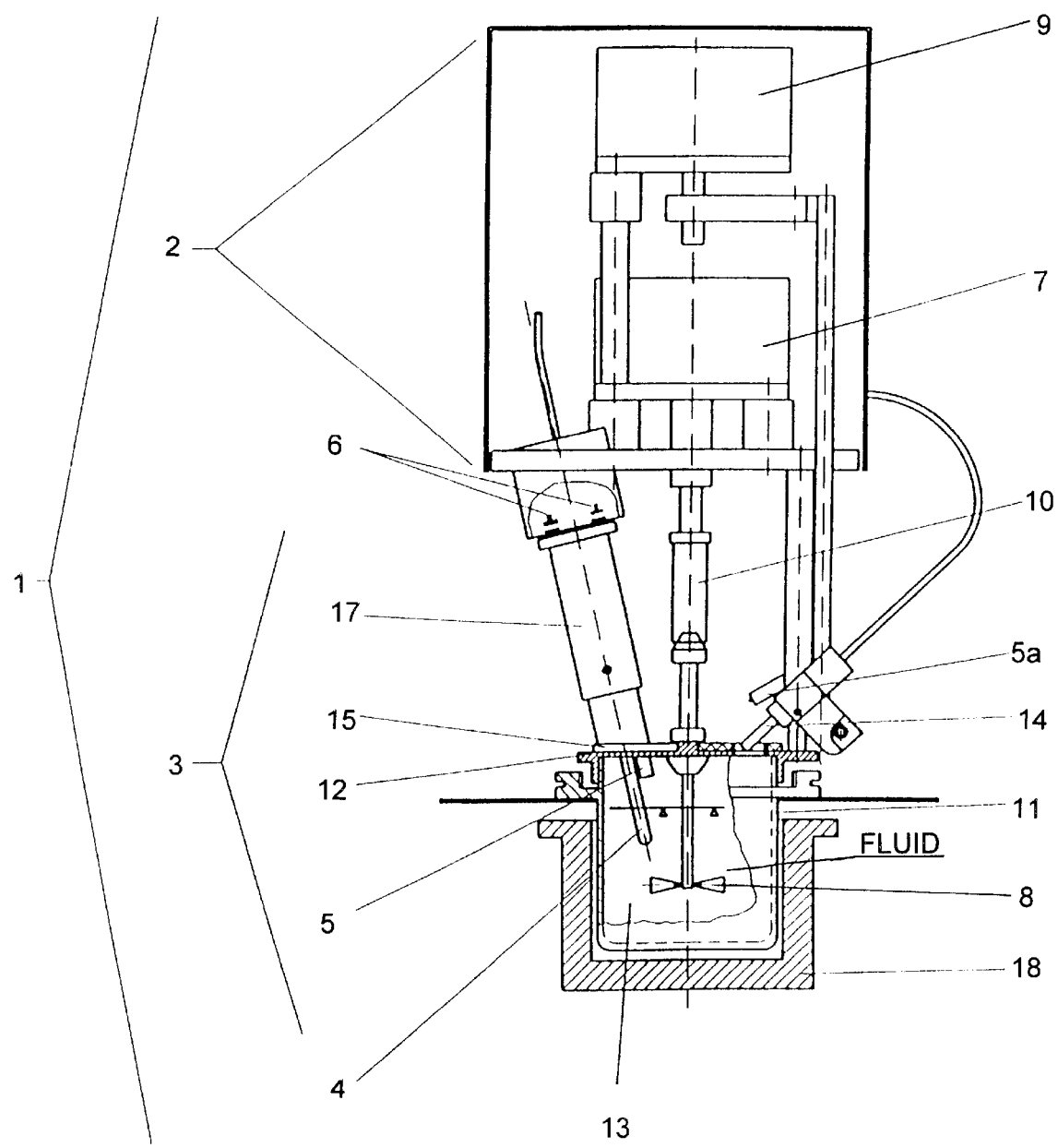
FIG. 2 shows a diagrammatic representation of the test insert and the simultaneous function head, which are connected to one another (flash point test phase).

In the present example, the ignition device 14 is also disposed on the simultaneous function head 2 in such a manner that, when the simultaneous function head 2 is connected with the test insert 3, it dips into the ignition opening 16, as can be seen in FIG. 2. In addition, an additional flash point indicator 5a, which makes possible an additional indication above the immersed ignition flame and, with that, outside of the test insert 3 as a whole, is disposed in the present example above the ignition opening 16. The realization can also be accomplished by a thermal indication or also, for example, by automatically observing the inflammation at this site. This inflammation outside of the test insert 3 occurs, for example, as a result of a high vapor pressure in the test insert 3 or as a result of a late start for the ignition (under some circumstances, the liquid is already boiling). It is not ensured here that the inflammation of the ignited vapor mixture strikes back into the test insert 3 and, with that, can be noted by the conventional indication by way of the flash point indicator 5.

In a further example, which is not shown in the Figures, the igniter 14 is also disposed at the test insert 3 and has connecting elements for connection to the simultaneous function head 2 or directly to the supply media, such as gas and/or electrical energy. In the case of this variation of the embodiment, the rotary slide valve 15, the rotary slide valve driving mechanism 9 and the manipulating element 9a can optionally be omitted.

The mode of functioning of the test equipment as a whole is described in the following in the time sequences, in which it takes place. After the test vessel 11 is filled with the test liquid 13, the test insert 3 is closed off in the standard manner by the test lid 12 with the rotary slide valve 15 and the sleeve 17 with the temperature sensor 4 and the flash point indicator 9. The arrangement is placed in the thermostatting equipment 18. The simultaneous function head 2 is now set down manually or also by means of an automatic driving mechanism. With this, all the necessary connections and positionings are made automatically. In detail, these are the electrical contacts for transferring the measured sample temperature and the flash point indication. Furthermore, the igniter, which has meanwhile been removed from the test lid, is placed into the required starting position (alternatively, the igniter can remain on the test lid, in which case it must be possible to detach the supply connections when exchanging the test insert) and the frictional connection from the stirrer driving mechanism 7 to the stirrer 8 is established and the manipulating element 9a of the rotary slide valve driving mechanism 9 for opening and closing the rotary slide valve 15 is positioned.

The invention is not limited to the examples shown here. Rather, by a suitable combination of the means and distinguishing features shown, it is possible to realize further variations of the embodiments, without leaving the scope of the invention.

We claim:

1. A method for determining the flash point of a liquid, comprising the steps of, in sequence:

(a) filling a test vessel with the liquid, closing the vessel with a lid, the vessel comprising a temperature measuring means, a flash point measuring means, a rotary valve means for opening and closing the lid, and stirring means, the vessel and liquid together forming a test insert, (b) placing the test insert within a thermostatting means, (c) connecting the test insert with a multiple function means, comprising means for operating the valve means, means for rotating the stirring means, and electrical conducting means for transferring measurements from the temperature measuring means and the flash point measuring means, (d) effecting a flash point measurement operation, comprising measuring the flash point both inside the vessel, and outside the vessel at a point above an ignition opening in the lid, (e) disconnecting the test insert from the simultaneous function means, (f) removing the test insert from the thermostatting means.

2. The method of claim 1, further comprising the step of, before completion of step (f), preparing a second test insert according to step (a) for placing within the thermostatting means for flash point measurement upon removal of a first test insert from the thermostatting means.

3. The method of claim 1, wherein the vessel further comprises ignition means and the multiple function means further comprises a means for powering the ignition means.

4. The method of claim 1, wherein the multiple function means is movable relative to the thermostatting means, and the connecting step is accomplished by moving the multiple function means into a connected position with respect to the test insert.

5. An apparatus for determining the flash point of a liquid, comprising a thermostatting means, a test insert, the test insert comprising a vessel for receiving a liquid, the vessel comprising a lid, temperature measuring means, a flash point measuring means, a rotary valve means for opening and closing the lid, and stirring means, a multiple function head, the multiple function head comprising means for operating the valve means, means for rotating the stirring means, and electrical conducting means for transferring measurements from the temperature measuring means and the flash point measuring means, comprising means for measuring the flash point both inside the vessel, and outside the vessel at a point above an ignition opening in the lid, wherein the test insert is removably insertable in the thermostatting means, and the multiple function head is removably connectable to the test insert.

6. The apparatus of claim 5, wherein the multiple function head is movable relative to the test insert while the multiple function head is in a disconnected position with respect to the test insert.

7. The apparatus of claim 6, wherein the multiple function head is movable along a fixed path so as to bring the multiple function head alternatively into a connected position and a disconnected position with respect to the test insert.

8. The apparatus of claim 5, wherein the test insert is freely removable with respect to the thermostatting means.

9. The apparatus of claim 5, further comprising a plurality of test inserts.

10. The apparatus of claim 5, wherein the test insert further comprises ignition means, and the multiple function means further comprises means for powering the ignition means.

* * * * *